US00PP30768P2

(12) United States Plant Patent
Vlielander

(10) Patent No.: US PP30,768 P2
(45) Date of Patent: Jul. 30, 2019

(54) ***KALANCHOE* PLANT NAMED 'DOKALNOL'**

(50) Latin Name: *Kalanchoe blossfeldiana*
Varietal Denomination: Dokalnol

(71) Applicant: DUMMEN GROUP B.V., De Lier (NL)

(72) Inventor: Ike J. Vlielander, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/932,280

(22) Filed: Feb. 16, 2018

(51) Int. Cl.
*A01H 5/02* (2018.01)

(52) U.S. Cl.
USPC ..... Plt./338

(58) Field of Classification Search
USPC ..... Plt./338
CPC ..... A01H 5/02; A01H 5/0266; A01H 6/32
See application file for complete search history.

*Primary Examiner* — June Hwu
(74) *Attorney, Agent, or Firm* — C. A. Whealy

(57) ABSTRACT

A new and distinct cultivar of *Kalanchoe* plant named 'Dokalnol', characterized by its compact, upright and uniformly mounded plant habit; moderately vigorous growth habit; freely branching plant habit; glossy dark green-colored leaves; uniform, early and freely flowering habit; large double bright yellow orange-colored flowers; and excellent postproduction longevity.

2 Drawing Sheets

Botanical designation: *Kalanchoe blossfeldiana.*
Cultivar denomination: 'DOKALNOL'.

BACKGROUND OF THE INVENTION

The present invention relates to a new and distinct *Kalanchoe* plant, botanically known as *Kalanchoe blossfeldiana* and hereinafter referred to by the name 'Dokalnol'.

The new *Kalanchoe* is a product of a planned breeding program conducted by the Inventor in De Lier, The Netherlands. The objective of the breeding program is to create new freely-branching and freely-flowering *Kalanchoe* plants with attractive leaf and flower coloration.

The new *Kalanchoe* plant originated from a cross-pollination made by the Inventor in De Lier, The Netherlands in April, 2011 of a proprietary selection of *Kalanchoe blossfeldiana* identified as code number 5545-01, not patented, as the female, or seed, parent with a proprietary selection of *Kalanchoe blossfeldiana* identified as code number 6188-03, not patented, as the male, or pollen, parent. The new *Kalanchoe* plant was discovered and selected by the Inventor as a single flowering plant from within the progeny of the stated cross-pollination in a controlled environment in De Lier, The Netherlands in May, 2012.

Asexual reproduction of the new *Kalanchoe* plant by vegetative terminal cuttings in a controlled environment in De Lier, The Netherlands since 2012 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalnol'. These characteristics in combination distinguish 'Dokalnol' as a new and distinct *Kalanchoe* plant:

1. Compact, upright and uniformly mounded plant habit.
2. Moderately vigorous growth habit.
3. Freely branching plant habit.
4. Glossy dark green-colored leaves.
5. Uniform, early and freely flowering habit.
6. Large double bright yellow orange-colored flowers.
7. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are more freely branching than plants of the female parent selection.
2. Plants of the new *Kalanchoe* have smaller leaves than plants of the female parent selection.
3. Plants of the new *Kalanchoe* flower earlier than plants of the female parent selection.
4. Plants of the new *Kalanchoe* and the female parent selection differ in flower color as plants of the female parent selection have dull yellow orange-colored flowers.

Plants of the new *Kalanchoe* can be compared to plants of the male parent selection. Plants of the new *Kalanchoe* differ from plants of the male parent selection in the following characteristics:

1. Plants of the new *Kalanchoe* are more compact than plants of the male parent selection.
2. Plants of the new *Kalanchoe* are more freely branching than plants of the male parent selection.
3. Plants of the new *Kalanchoe* have larger flowers than plants of the male parent selection.
4. Plants of the new *Kalanchoe* and the male parent selection differ in flower color as flowers of plants of the male parent selection are dull yellow in color.

Plants of the new *Kalanchoe* can be compared to plants of the *Kalanchoe blossfeldiana* 'Brazil', not patented. In side-by-side comparisons, plants of the new *Kalanchoe* differ primarily from plants of 'Brazil' in the following characteristics:

1. Plants of the new *Kalanchoe* are more freely branching than plants of 'Brazil'.
2. Plants of the new *Kalanchoe* have larger flowers than plants of 'Brazil'.
3. Plants of the new *Kalanchoe* flower earlier than plants of 'Brazil'.
4. Plants of the new *Kalanchoe* and 'Brazil' differ in flower color as flowers of plants of 'Brazil' are light yellow orange in color.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet is a side perspective view of a typical flowering plant of 'Dokalnol' grown in a container.

The photograph on the second sheet is a close-up view of a typical open flower and flower buds of 'Dokalnol'.

DETAILED BOTANICAL DESCRIPTION

The aforementioned photographs and following observations, measurements and values describe plants grown during the autumn in 10-cm containers in a glass-covered greenhouse in De Lier, The Netherlands and under cultural practices typical of commercial *Kalanchoe* production. During the production of the plants, day temperatures ranged from 20° C. to 22° C., night temperatures ranged from 19° C. to 21° C. and light levels ranged from 10,000 lux to 55,000 lux. Plants received long day/short night conditions (more than 14 hours of light) for three weeks then plants received photoinductive short day/long night conditions (minimum 14 hours darkness) until flowering. Plants were 16 weeks old when the photographs were taken and 17 weeks old when the description was taken. In the detailed description, color references are made to The Royal Horticultural Society Colour Chart, 2007 Edition, except where general terms of ordinary dictionary significance are used.

Botanical classification: *Kalanchoe blossfeldiana* 'Dokalnol'.

Parentage:

*Female, or seed, parent*.—Proprietary selection of *Kalanchoe blossfeldiana* identified as code number 5545-01, not patented.

*Male or pollen parent*.—Proprietary selection of *Kalanchoe blossfeldiana* identified as code number 6188-03, not patented.

Propagation:

*Type*.—By vegetative terminal cuttings.

*Time to initiate roots, summer*.—About eleven days at temperatures about 21° C.

*Time to initiate roots, winter*.—About 16 days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; typically greyish white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright and uniformly mounded plant habit; freely flowering habit with numerous cymes positioned above the foliar plane; triangular in shape with rounded crown; appropriate for 10 to 15-cm containers; moderately vigorous growth habit.

*Plant height at flowering*.—About 16 cm.

*Plant diameter at flowering*.—About 17 cm.

*Branching habit*.—Freely branching habit with about five to eight lateral branches developing per plant; pinching (removal of the terminal apex) is not required but will enhance lateral branch development.

Lateral branch description:

*Length*.—About 10 cm to 14 cm.

*Diameter*.—About 2 mm to 4 mm.

*Internode length*.—About 2 cm to 4 cm.

*Aspect*.—Mostly upright.

*Strength*.—Moderately strong.

*Texture*.—Smooth, glabrous.

*Color*.—Close to 138A.

Leaf description:

*Arrangement*.—Opposite, simple; generally symmetrical.

*Quantity per plant*.—Typically about six to ten mature leaves and about six to nine generative (developing) leaves.

*Length*.—About 9.5 cm.

*Width*.—About 6.5 cm.

*Shape*.—Ovate.

*Apex*.—Obtuse.

*Base*.—Obtuse.

*Margin*.—Lobed, lobes vault-shaped.

*Texture and luster, upper and lower surfaces*.—Smooth, glabrous; coriaceous; succulent; glossy.

*Venation pattern*.—Pinnate.

*Color*.—Developing and fully developed leaves, upper surface: Close to 147A; venation, close to 147A. Developing and fully developed leaves, lower surface: Close to 146A; venation, close to 146A.

*Petioles*.—Length: About 1 cm. Diameter: About 4 mm to 8 mm. Texture, upper and lower surfaces: Smooth, glabrous; coriaceous; succulent. Color, upper surface: Close to 147A. Color, lower surface: Close to 146A.

Flower description:

*Flower arrangement and habit*.—Double-type flowers arranged in axillary cymes; uniform and freely flowering habit with usually more than 25 open flowers and more than 25 flower buds per lateral branch and more than 150 open flowers and flower buds developing per plant; plants flower continuously for at least seven weeks.

*Fragrance*.—None detected.

*Natural flowering season*.—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Early flowering habit, under short day/long night photoinductive conditions, plants begin flowering about nine to eleven weeks; actual time to flower is primarily dependent upon temperature and light intensity.

*Post-production longevity*.—Excellent post-production longevity; plants maintain good foliage and flower substance for about 48 days under interior conditions; individual flowers last about 20 days on the plant; flowers persistent.

*Flower diameter*.—About 2 cm.

*Flower length* (*height*).—About 1.2 cm.

*Flower buds*.—Shape: Rounded. Color, before flower opening: Close to 4D and 14C.

*Petals*.—Arrangement: About 24 to 28 in numerous whorls. Length: About 6 mm to 8 mm. Width: About 4 mm to 6 mm. Aspect: Flat to slightly upright. Shape: Ovate. Apex: Acute. Base: Obtuse. Margin: Entire. Texture and luster, upper and lower surfaces: Smooth, glabrous; shiny. Color: When opening, upper surface: Close to 6B. When opening, lower surface: Close to 6D. Fully opened, upper surface: Close to 16A; color becoming closer to 6C with development. Fully opened, lower surface: Close to 16D; color does not change with development.

*Petaloids*.—Arrangement: If present, about six at the center of the flower. Length: About 3 mm to 5 mm. Width: About 0.5 mm to 2.5 mm. Aspect: Upright and twisting. Shape: Elliptical, occasionally irregularly-shaped. Apex: Acute. Base: Obtuse. Margin: Entire. Texture and luster, upper and lower surfaces: Smooth, glabrous; shiny. Color: When opening, upper surface: Close to 6B. When opening, lower surface: Close to 6D. Fully opened, upper surface: Close to 16A; color becoming closer to 6C with development. Fully opened, lower surface: Close to 16D; color does not change with development.

*Sepals*.—Appearance: Four in a single whorl. Length: About 8 mm. Width: About 1.5 mm. Shape: Oblong, pointed. Apex: Acute. Base: Obtuse. Margin: Entire. Aspect: Upright, rigid. Texture and luster, upper and lower surfaces: Smooth; glabrous; shiny. Color, upper and lower surfaces: Close to 138B.

*Peduncles*.—Length: About 3 mm to 5 mm. Diameter: About 2 mm. Aspect: Erect, rigid. Strength: Strong. Texture: Smooth, glabrous. Color: Close to 138B.

*Reproductive organs*.—Androecium: Stamen number: If not transformed into petaloids, one to eight per flower. Anther shape: Elliptic, flat. Anther length: About 0.3 mm. Anther color: Close to 150D. Amount of pollen: Scarce. Pollen color: Close to 12A. Gynoecium: Pistil number: About four to eight. Pistil length: About 1 cm. Style length: About 7 mm. Style color: Close to 138D. Stigma shape: Flat. Stigma color: Close to 8D. Ovary color: Close to 138D.

*Seeds*.—Length: About 0.1 mm. Diameter: About 0.05 mm. Color: Close to 166C.

Temperature tolerance: Plants of the new *Kalanchoe* have been observed to tolerate temperatures from about 16° C. to about 35° C.

Pathogen & pest resistance: Plants of the new *Kalanchoe* have not been observed to be resistant to pests and pathogens common to *Kalanchoe* plants to date.

It is claimed:

1. A new and distinct *Kalanchoe* plant named 'Dokalnol' as illustrated and described.

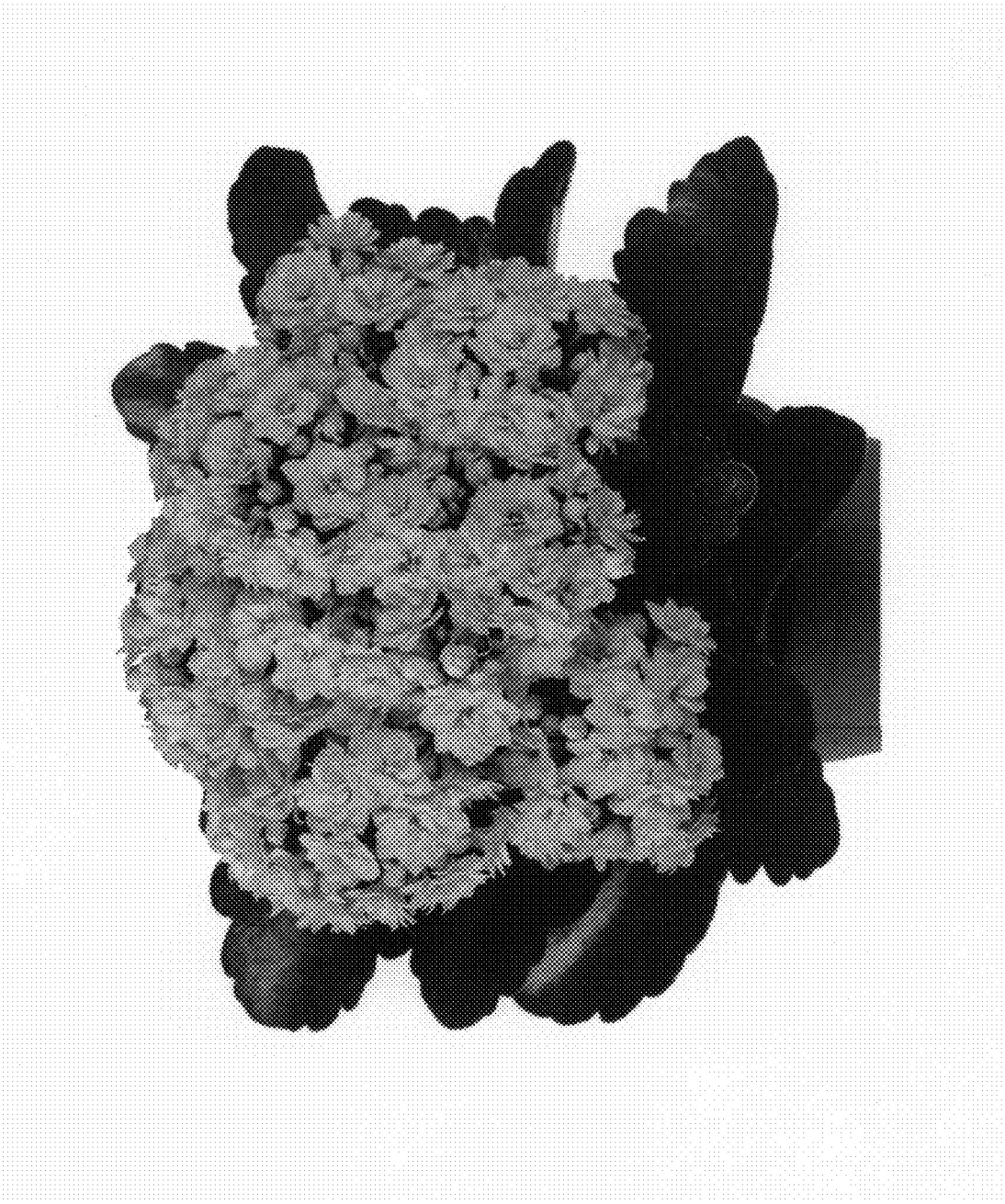

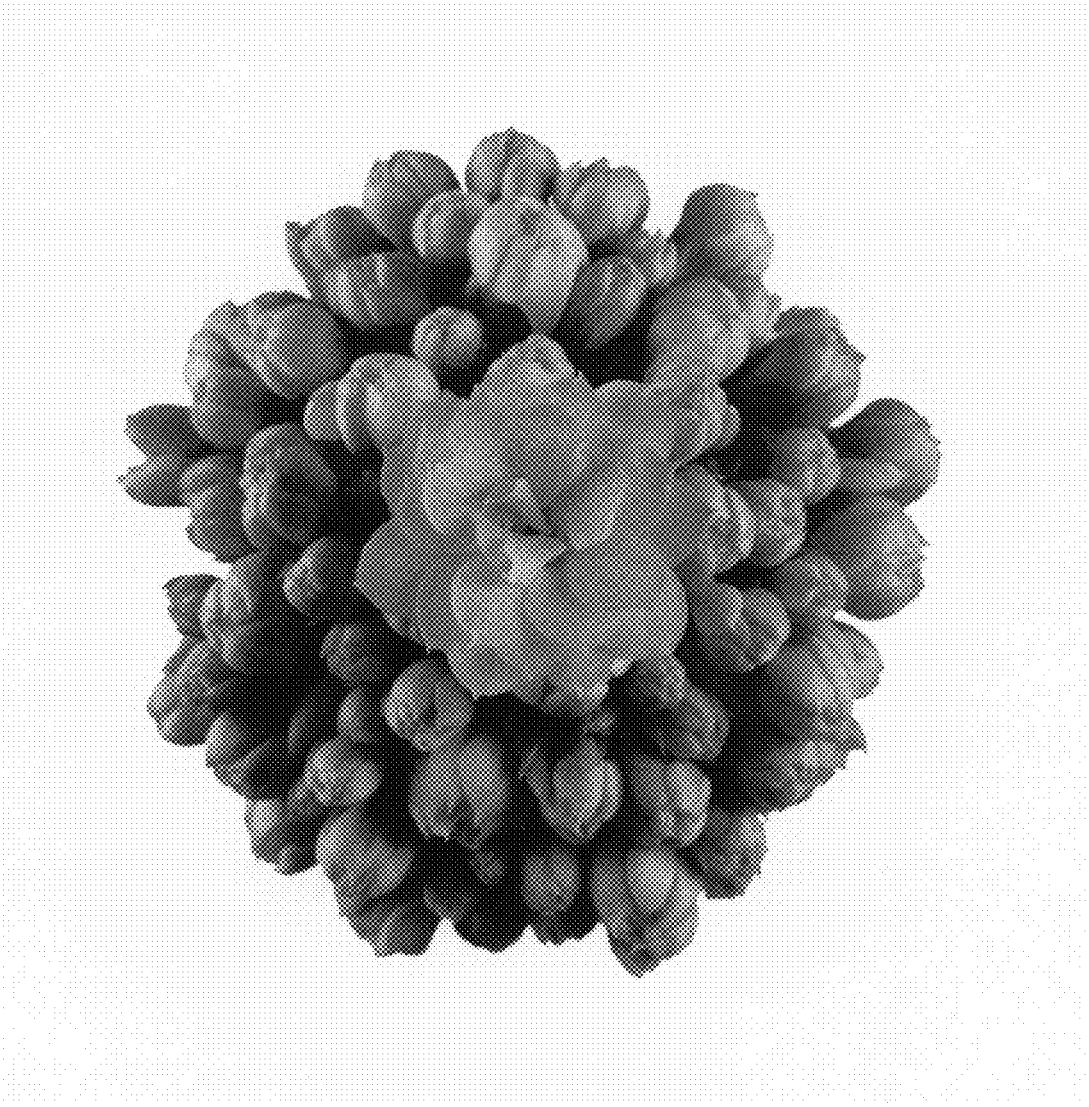

* * * * *